(12) United States Patent
McWeeney

(10) Patent No.: US 6,887,215 B2
(45) Date of Patent: May 3, 2005

(54) COMPRESSIBLE URETERAL STENT FOR COMFORT

(75) Inventor: John O. McWeeney, Brighton, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 84 days.

(21) Appl. No.: 10/006,083

(22) Filed: Dec. 6, 2001

(65) Prior Publication Data

US 2002/0183852 A1 Dec. 5, 2002

Related U.S. Application Data

(60) Provisional application No. 60/295,465, filed on Jun. 1, 2001.

(51) Int. Cl.[7] .................................................. A61F 2/04
(52) U.S. Cl. ........................................ 604/9; 623/23.68
(58) Field of Search ........................... 623/23.64, 23.66, 623/23.68, 23.7, 23.65, 23.69, 14.13; 604/8, 9; 600/30

(56) References Cited

U.S. PATENT DOCUMENTS

| 4,225,979 A | 10/1980 | Rey et al. |
| 4,334,327 A | 6/1982 | Lyman et al. |
| 4,531,933 A | 7/1985 | Norton et al. |

(Continued)

FOREIGN PATENT DOCUMENTS

| EP | 0490325 A1 | 6/1992 |
| EP | 1066804 A2 A3 | 1/2001 |
| WO | WO 99/18888 | 4/1999 |
| WO | 00/51521 | 9/2000 |
| WO | 00/66032 | 11/2000 |

OTHER PUBLICATIONS

PCT International Search Report for International Patent Application No. PCT/US02/14703, dated Oct. 3, 2002.

*Primary Examiner*—David H. Willse

(57) ABSTRACT

In one embodiment, the invention is directed to a ureteral stent adapted for placement within a patient's urinary tract to facilitate drainage from the patient's kidney to the patient's bladder. The ureteral stent includes an elongated portion, a retention portion and a mesh or coil portion. The elongated portion has first and second ends, defines an elongated portion of a lumen extending between the first and second ends, and has a length sufficient to extend within the ureter from the patient's kidney to the patient's bladder. The retention portion extends from the first end of the elongated portion, defines a retention portion of the lumen and at least one through aperture for providing fluid communication between the lumen and the kidney. The retention portion is adapted for placement substantially within the kidney and for retaining the placement of the stent within the kidney. The mesh or coil portion extends from the second end of the elongated portion and is adapted for placement substantially within an intramural tunnel portion of the ureter and for extension into the bladder. The mesh or coil portion is collapsible under radial compression to inhibit urine back flow to the kidney.

37 Claims, 10 Drawing Sheets

U.S. PATENT DOCUMENTS

| | | |
|---|---|---|
| 4,931,037 A | 6/1990 | Wetterman |
| 5,019,090 A | 5/1991 | Pinchuk |
| 5,019,102 A | 5/1991 | Hoene |
| 5,151,105 A | 9/1992 | Kwan-Gett |
| 5,160,341 A | 11/1992 | Brenneman et al. |
| 5,224,953 A | 7/1993 | Morgentaler |
| 5,282,860 A | 2/1994 | Matsuno et al. |
| 5,380,270 A | 1/1995 | Ahmadzadeh |
| 5,599,291 A | 2/1997 | Balbierz et al. |
| 5,749,921 A | 5/1998 | Lenker et al. |
| 5,755,772 A | 5/1998 | Evans et al. |
| 5,766,209 A | 6/1998 | Devonec |
| 5,876,445 A | 3/1999 | Andersen et al. |
| 5,879,381 A | 3/1999 | Moriuchi et al. |
| 5,964,744 A | 10/1999 | Balbierz et al. |
| 5,968,070 A | 10/1999 | Bley et al. |
| 5,968,088 A | 10/1999 | Hansen et al. |
| 6,013,854 A | 1/2000 | Moriuchi |
| 6,165,210 A | 12/2000 | Lau et al. |
| 6,165,211 A | 12/2000 | Thompson |
| 6,183,503 B1 | 2/2001 | Hart et al. |
| 6,197,014 B1 | 3/2001 | Samson et al. |
| 6,214,037 B1 | 4/2001 | Mitchell et al. |
| 6,238,431 B1 | 5/2001 | Asimacopoulos |
| 6,253,443 B1 | 7/2001 | Johnson |
| 6,395,021 B1 * | 5/2002 | Hart et al. ............... 623/1.15 |
| 2001/0053936 A1 | 12/2001 | Whitmore, III |

* cited by examiner (BACKGROUND)

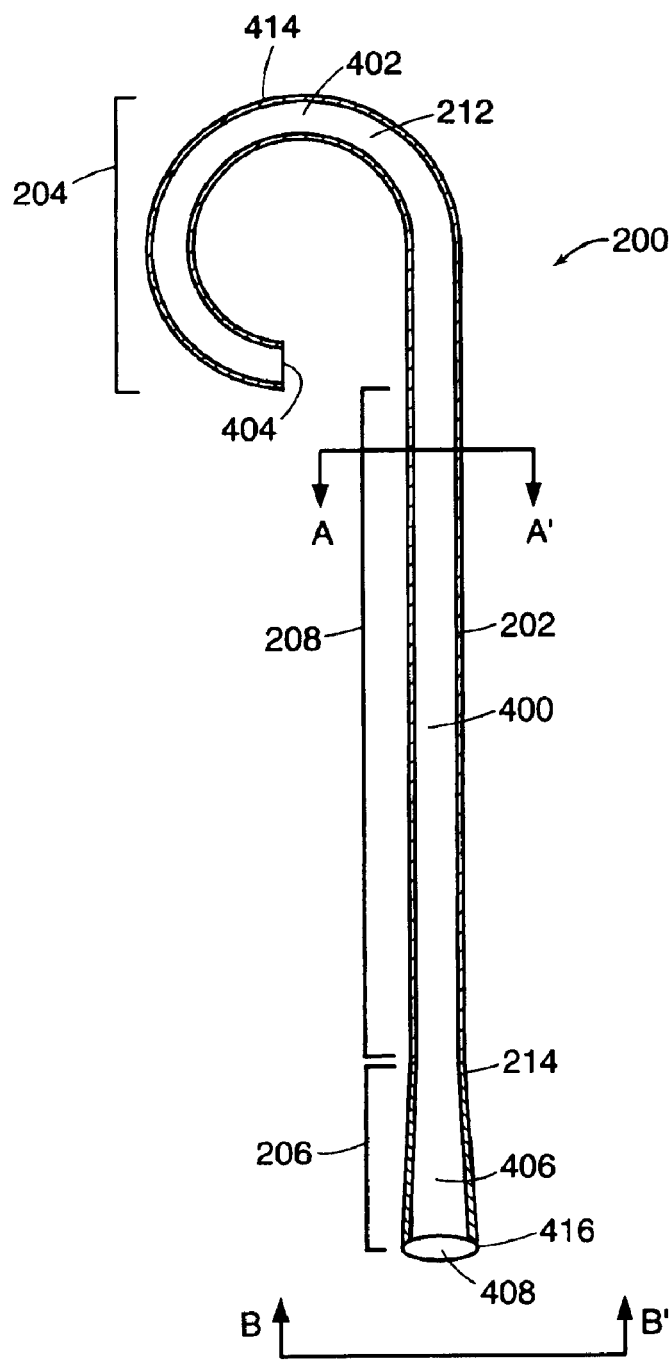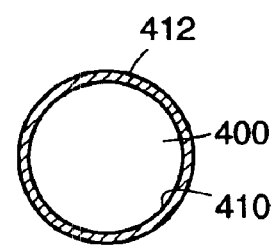
FIG. 4B
FIG. 4A

US 6,887,215 B2

COMPRESSIBLE URETERAL STENT FOR COMFORT

CROSS-REFERENCE TO RELATED CASE

This application claims priority to and the benefit of the U.S. provisional patent application Ser. No. 60/295,465, filed on Jun. 1, 2001, the entirety of which is incorporated herein by reference.

TECHNICAL FIELD

This invention generally relates to ureteral stents. More particularly in one embodiment, the invention is directed to a ureteral stent having a bladder end adapted to reduce patient discomfort.

BACKGROUND INFORMATION

A stent is a medical device provided for propping open an obstructed passage within the body, such as a blocked ureter. In general, ureteral blockage is a medical condition requiring treatment. A ureteral blockage can occur for a number of reasons, including the passage of a kidney stone and/or other material into the ureter where it becomes entrapped. Also, a tumor growing against the outer wall of the ureter can force compression or constriction of the ureter. A tumor on the internal ureteral wall can also cause blockage of the ureter. Ureteral stents are often used to correct such problems. A ureteral stent may be placed inside the ureter on a temporary basis to allow proper drainage of fluids from the kidney to the bladder. A ureteral stent usually comprises a straight length of hollow tubing with each end having a hook or a curl or other configuration for preventing migration or expulsion of the stent from its placed position within the ureter. One end of a typical ureteral stent is placed in the kidney and the other end is placed in the bladder. The end positioned in the kidney is typically configured to retain the stent within the renal pelvis and to prevent the downward migration of the stent into the ureter. The bladder end of the stent is typically configured to prevent upward migration of the stent towards the kidney.

FIG. 1 is a conceptual background drawing showing a portion of the human urinary tract. Referring to FIG. 1, in a human urinary tract 100, the ureters 102 and 104 transport urine from the kidneys 106 and 108 to the bladder 110. The trigone region of the bladder 112 is located between the urethral opening 114 and the two ureteral orifices 116 and 118. The pain associated with an in-dwelling ureteral stent is attributable in-part to contact between the stent and the bladder mucosa 120 in the trigone region 112. The trigone region 112 is believed to be particularly innervated and sensitive to the presence of any foreign bodies such as the bladder end of a ureteral stent. The intramural tunnel regions 122 and 124 of the ureters 102 and 104, respectively, act like valves, shutting off to prevent back flow of urine from the bladder 112 to the kidneys 106 and 108. The intramural tunnel regions 122 and 124 are also believed to be particularly innervated and sensitive to the presence of any foreign bodies. In addition, further discomfort due to in-dwelling stents can be caused by flank pain due to urine shooting from the bladder 110 back up the ureters 102 and 104 intra-luminally via the stent, and/or extra-luminally around the stent.

SUMMARY OF THE INVENTION

The invention generally relates to ureteral stents, particularly those that reduce (compared with conventional ureteral stents) patient discomfort when the stent is placed within the patient's body. One object of the invention is to keep the ureteral passage open to allow the flow of fluids from the kidney to the bladder. Another object of the invention is to reduce, minimize or avoid patient discomfort associated with conventional in-dwelling ureteral stents by reducing irritation of the trigone region of the bladder mucosa.

In one embodiment, the invention is directed to a ureteral stent including an elongated portion, a retention portion for placement substantially within a kidney, and a collapsible portion for placement substantially within the intramural tunnel portion of a ureter and extending into the bladder. The elongated portion of the stent has a lumen which extends along the length of the ureter from the kidney to the bladder. According to one feature, the retention portion extends from a first end of the elongated portion and is configured to be retained within the kidney. According to another feature, the collapsible portion extends from a second end of the elongated portion, and it is collapsible under radial compression from the intramural tunnel region to inhibit back flow of urine to the kidney.

In one embodiment, the collapsible portion is fabricated from a mesh material. In another embodiment, the collapsible portion is fabricated from a wound coil. According to one feature, the collapsible portion includes an outer coating of a biocompatible material adapted to avoid tissue ingrowth. According to another feature, the collapsible portion includes an inner lining adapted to avoid urine encrustation on an inner surface of a lumen formed by the collapsible portion which extends from the lumen formed by the elongated portion of the stent.

In another aspect, the invention relates to methods of inserting into a patient one of the ureteral stents mentioned above. One method includes the step of passing a guide wire through the ureter and into the kidney, and thereafter coaxially sliding a stent over the guide wire and into the ureter by using a tubular stent pusher. One alternate method includes placing a stent with a closed kidney end over a guide wire, and then advancing the stent into the ureter by pushing the guide wire. According to another embodiment, the stent is inserted from the kidney downward through the ureter and into the bladder.

In yet other aspects, the invention features methods of manufacturing stents such as the ureteral stents mentioned above.

The foregoing and other objects, aspects, features and advantages of the invention will become more apparent from the following description and from the claims.

BRIEF DESCRIPTION OF THE DRAWINGS

The foregoing and other objects of the invention and the various features thereof may be more fully understood from the following description when read together with the accompanying drawings in which like reference characters generally refer to the same parts throughout the different views and in which the depicted components are not necessarily drawn to scale:

FIG. 4A is a longitudinal, cross-sectional view of the stent of FIG. 2;

FIG. 4B is a transverse, cross-sectional view of the stent of 4A, taken along the line A–A';

ILLUSTRATIVE DESCRIPTION

Figure 1:
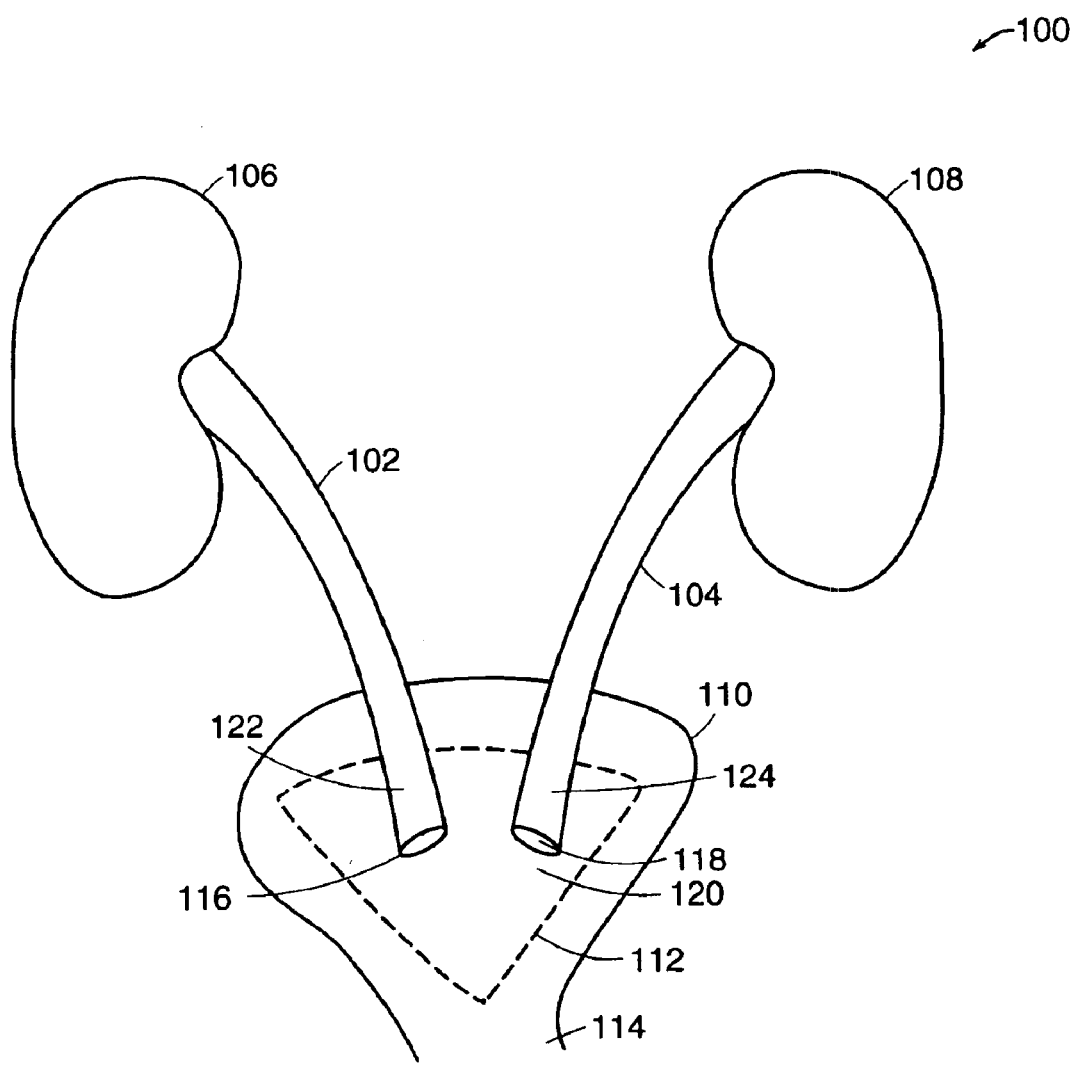
FIG. 1 is a schematic view of a human urinary tract.
Figure 2:
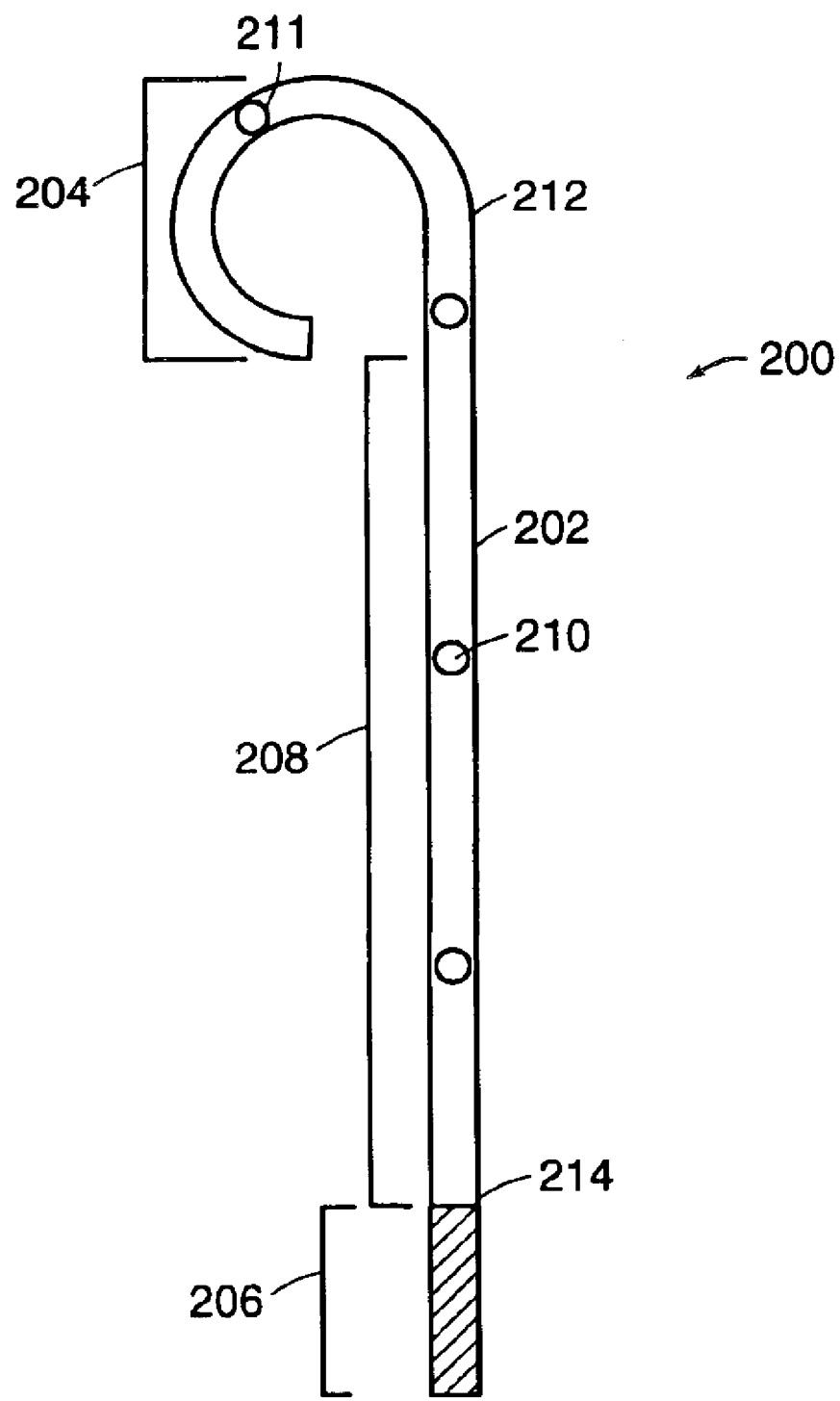
FIG. 2 is a schematic view of a ureteral stent according to an illustrative embodiment of the invention.
Figure 3A:
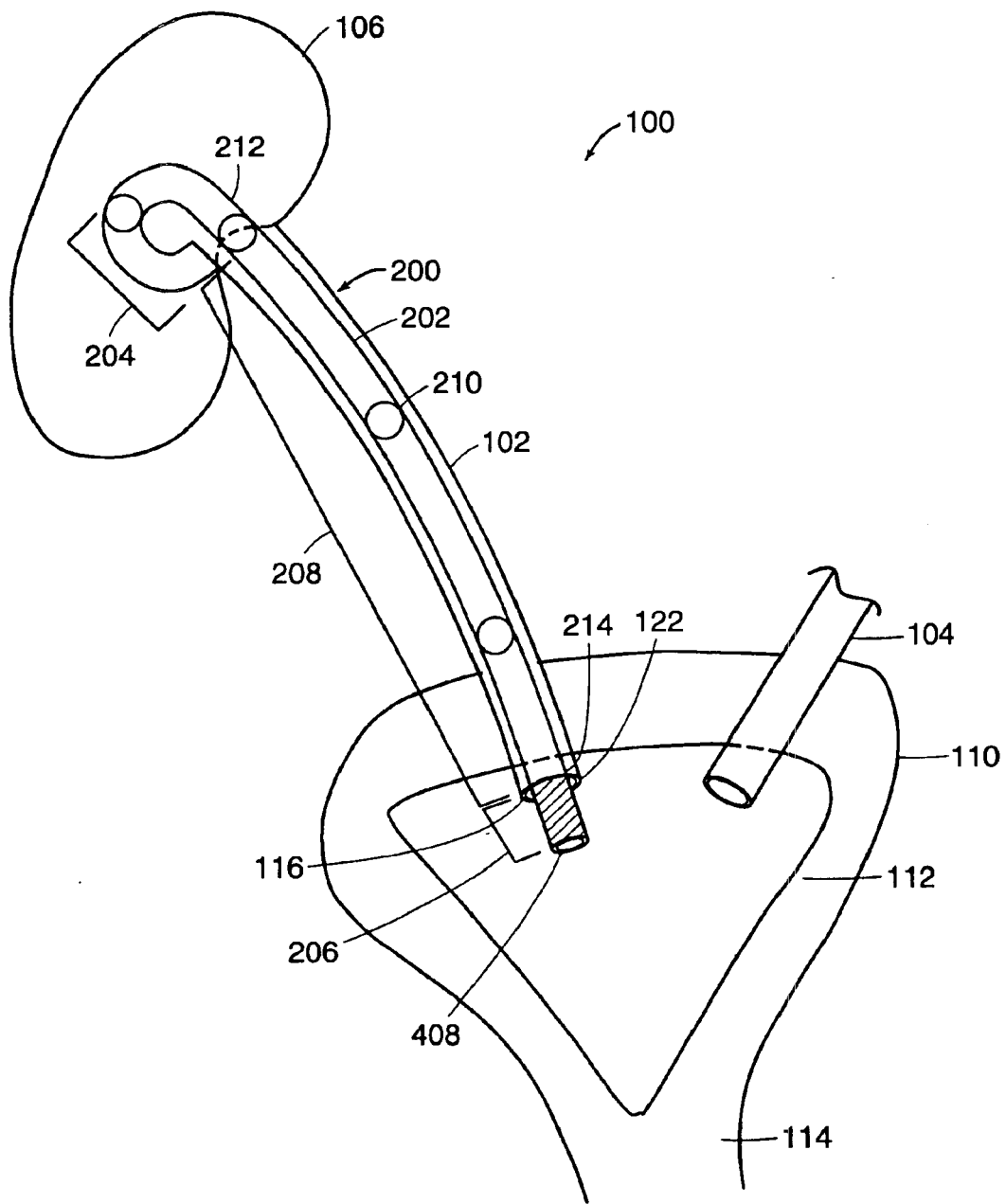
FIG. 3A is a schematic view of a ureteral stent according to an illustrative embodiment of the invention, and positioned within a human urinary tract.
Figure 3B:
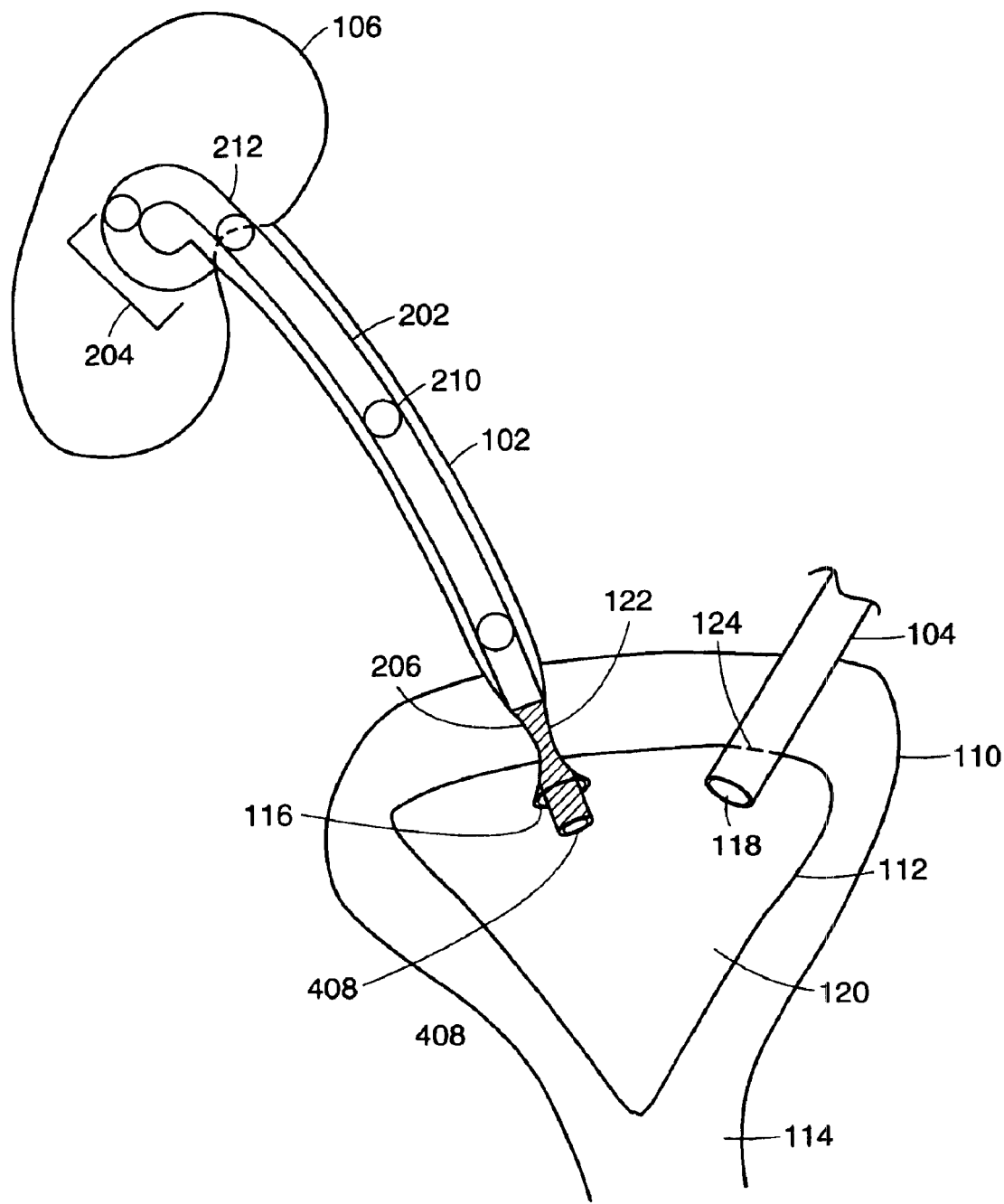
FIG. 3B is a schematic view of the stent of FIG. 3A, including an illustrative bladder end in a collapsed state.

As discussed above in summary, in one embodiment, the invention is directed to a ureteral stent having a bladder end adapted to reduce patient discomfort. FIG. 2 depicts a ureteral stent 200 in accordance with an illustrative embodiment of the invention. FIGS. 3A and 3B depict the ureteral stent 200 placed inside a human urinary tract 100. A skilled artisan will appreciate that a ureteral stent of the invention can be placed in either ureter 102 or 104. However, for simplicity, the following discussion is limited to placement of the ureteral stent 200 within the ureter 102. As depicted, the illustrative ureteral stent 200 includes an elongated portion 202, a retention portion 204, and a collapsible portion 206. The elongated portion 202 has a length 208 that is sufficient to extend through the ureter 102 from the kidney 106 to the bladder 110. The elongated portion 202 of the ureteral stent 200 defines a lumen (shown in FIGS. 4A and 4B at 400) extending from a kidney end 212 to a bladder end 214. According to the illustrative embodiment, the ureteral stent 200 also includes one or more through apertures or eye ports 210 located along the length of the elongated portion 202 for providing fluid communication between an outer wall (shown in FIGS. 4A and 4B at 412) and an inner lumen wall (shown in FIG. 4B at 410) to further enable drainage through the internal lumen 400 of the ureteral stent 200. According to one feature, the elongated portion 202 is made of a physiologically compatible material such as, for example, polyvinyl alcohol, polyethylene oxide, hydroxy ethyl cellulose, stainless steel, or the like.

The retention portion 204 extends from the kidney end 212 of the ureteral stent 200, and is adapted for placement substantially within the kidney 106, and for retention of the placement. According to one feature, the retention portion 204 includes one or more through apertures or eye ports 211 for providing fluid communication between an outer wall (shown at FIG. 4A at 414) and an inner lumen (shown in FIG. 4A at 402) to further enable drainage through the internal lumens 400 and 402.

The collapsible portion 206 extends from the bladder end 214 of the ureteral stent 200, and is adapted for residing substantially within the intramural tunnel region 122 of the ureter 102 and for extending into the bladder 110. According to an illustrative embodiment, the invention addresses reflex prevention and intramural tunnel irritation via the collapsible portion 206 of the ureteral stent 200.

FIG. 3A depicts the intramural tunnel region 122 in a relaxed state and the collapsible portion 206 of the ureteral stent 200 in an expanded and open state. As shown in FIG. 3B, as the intramural tunnel region 122 contracts radially, the collapsible portion 206 collapses to restrict urine back flow from bladder 110 to the kidney 106.

FIG. 4A is a schematic of a longitudinal, cross-sectional view of the ureteral stent 200. FIG. 4B is a lateral cross-sectional view of the length 208 of the elongated portion 202 taken along the view A–A'. As mentioned above, and as shown in FIGS. 4A and 4B, the elongated portion 202 of the ureteral stent 200 defines an internal lumen 400 that extends through the elongated portion 202 between the kidney end 212 and the bladder end 214. The retention portion 204 also defines an internal lumen 402 which extends from the lumen 400 of the elongated portion 202. The retention portion 204 includes at least one through aperture 404 adapted for providing fluid communication between the internal lumen 402 and the kidney 106.

The collapsible portion 206 also defines an inner lumen 406 which extends from the internal lumen 400 of the elongated portion 202. The inner lumen 406 terminates in at least one through aperture 408. As shown in FIGS. 3A and 3B, when placed in a patient, the through aperture 408 resides within the bladder 110 and is adapted for providing urine flow from the lumen 406 into the bladder 110.

Figure 5A:
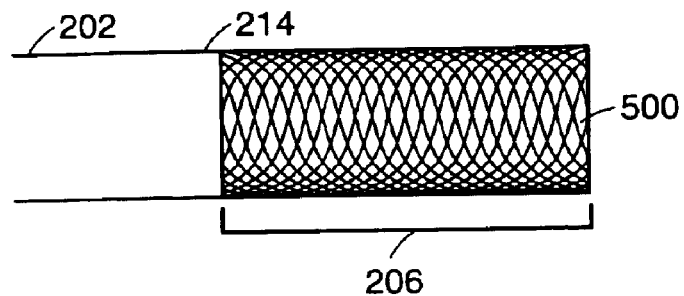
FIG. 5A is an enlarged side view of an illustrative collapsible mesh portion of a stent of FIG. 2, in an expanded and open state.
Figure 5B:
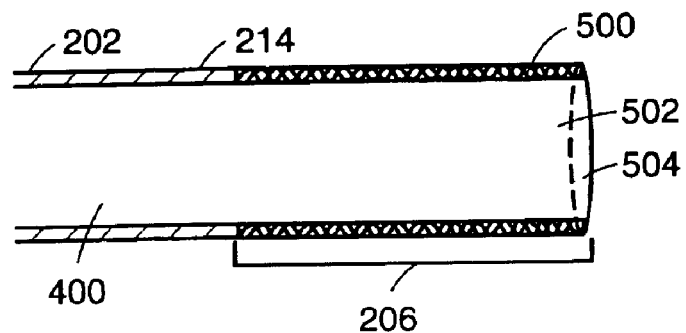
FIG. 5B is a longitudinal, cross-sectional view of the illustrative mesh portion of the stent of FIG. 5A, in an expanded and open state.
Figure 5C:
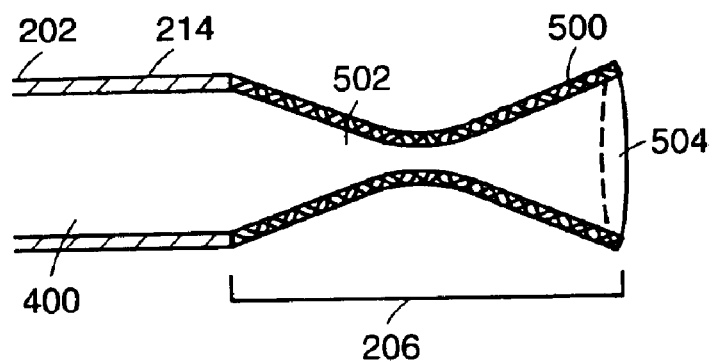
FIG. 5C is a longitudinal, cross-sectional view of the illustrative mesh portion of the stent of FIG. 5A, in a collapsed condition due to radial compression.

FIG. 5A depicts one illustrative embodiment in which the collapsible portion 206 of a ureteral stent 200 of the invention includes a mesh portion 500. Illustratively, the mesh portion 500 extends from the bladder end 214 of the elongated portion 202. In FIG. 5A, the mesh portion 500 is depicted in an expanded and open state. FIG. 5B is a longitudinal, cross-sectional view of the collapsible portion 206 of the stent of FIG. 5A in the expanded and open state. As shown, the mesh portion 500 forms an inner lumen 502 which extends from the internal lumen 400 of the elongated portion 202. The lumen 502 ends in at least one opening 504 which resides in the bladder 110 to allow fluid communication between the lumen 502 and the bladder 110. FIG. 5C is a longitudinal, cross-sectional view of the collapsible mesh portion 500, shown in a collapsed state. As discussed above, the collapsible portion 206 collapses, for example, due to a radial force exerted on the exterior of the mesh portion 500, and inhibits through fluid flow. In one illustrative embodiment, the mesh portion 500 is manufactured from polymeric or metallic materials such as, for example, stainless steel, tantalum, gold, titanium, nitinol, polytetrafluoroethylene (PTFE) or any suitable material that collapses under an exerted force of the type exerted by the intramural tunnel region 122 of the ureter 102, and returns to an expanded state upon removal of such a force. One advantage of the invention is that the collapsible mesh portion 500 of the ureteral stent 200 prevents fluid flow in response to radial force exerted by the intramural tunnel region 122 by collapsing to inhibit vesicourinal reflux, back flow of urine and flank pain in a patient.

Figure 6A:
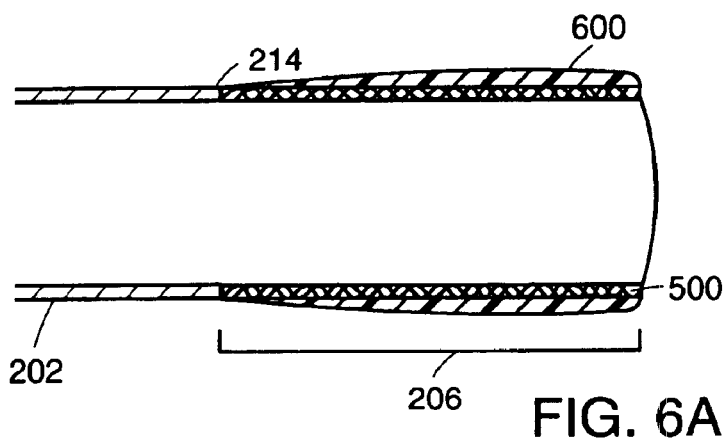
FIG. 6A is a longitudinal, cross-sectional view of the illustrative mesh portion of the stent of FIG. 5A, including an outer covering.
Figure 6B:
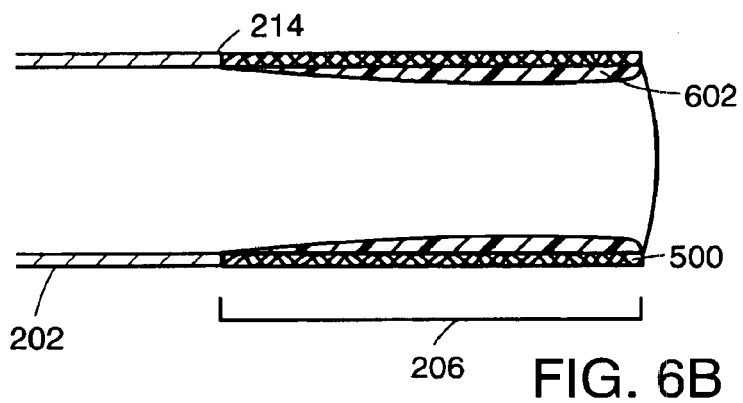
FIG. 6B is a longitudinal, cross-sectional view of the illustrative mesh portion of the stent of FIG. 5A, including an inner lining.
Figure 6C:
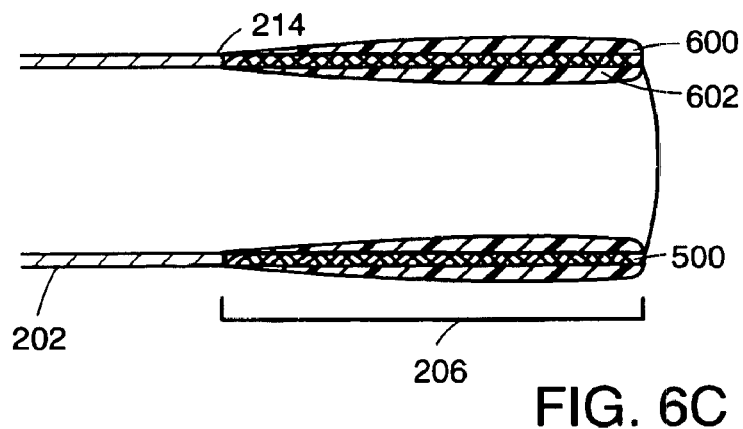
FIG. 6C is a longitudinal, cross-sectional view of the illustrative mesh portion of the stent of FIG. 5A, including both an inner lining and an outer covering.

FIGS. 6A–6C depict enlarged longitudinal, cross-sectional views, further illustrating embodiments of the mesh portion 500. As shown in FIG. 6A, in one illustrative embodiment, the collapsible mesh portion 500 has an outer covering 600. In the illustrative embodiment, the outer covering 600 is formed from a flexible polymer such as, for example, polyurethane, polyamide, silicone, polyvinyl chloride, or the like. As shown in FIG. 6B, in a further illustrative embodiment, collapsible mesh portion 500 has an inner lining 602 such as, for example, a jacket or a sleeve. In one embodiment, the inner lining 602 encases the interior of the mesh portion 500. The inner lining 602 functions to substantially prevent internal mesh encrustation due to urine contact. In the illustrative embodiment, the inner lining 602 is fabricated from a polymer such as, for example, polyurethane, polyamide, silicone, polyvinyl chloride, or the like.

In one preferred embodiment, the collapsible mesh portion 500 includes both an outer covering 600 as well as an inner lining 602. In the illustrative embodiment, the mesh portion 500 is sandwiched between an outer covering 600 and an inner lining 602, which encase the exterior and the interior of the mesh portion 500 respectively. In another embodiment, a polymer is interspersed within the mesh.

Figure 7A:
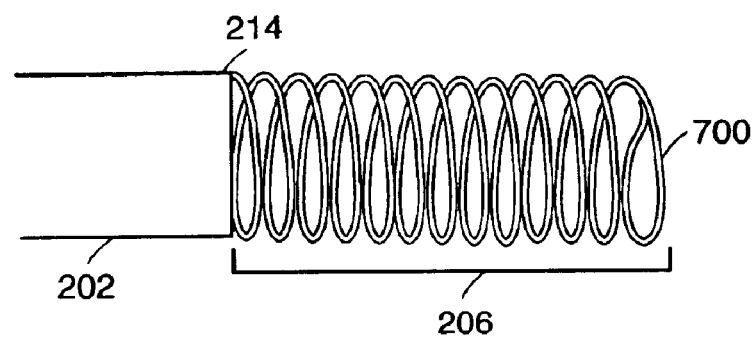
FIG. 7A is an enlarged side view of an illustrative collapsible wound coil portion of the stent of FIG. 2, in an expanded and open state.
Figure 7B:
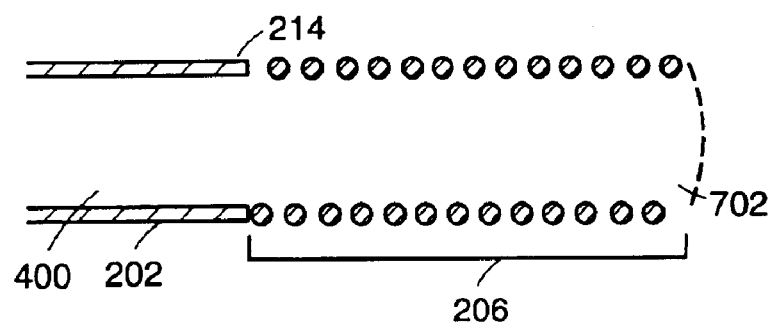
FIG. 7B is a longitudinal, cross-sectional view of the illustrative wound coil portion of the stent of FIG. 7A, in an expanded and open state.
Figure 7C:
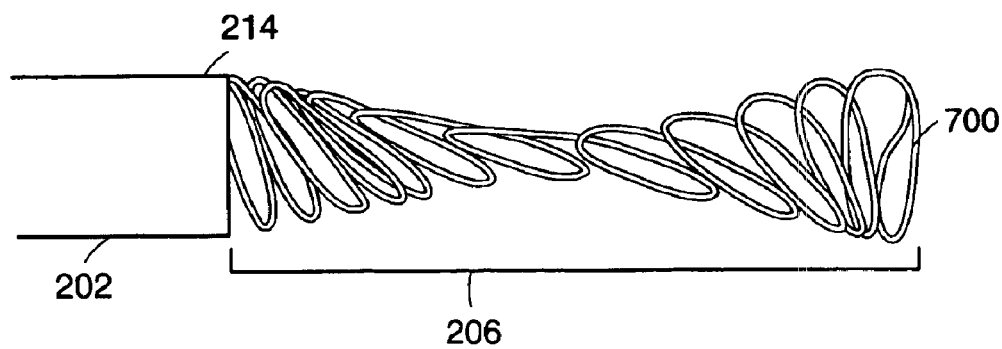
FIG. 7C is an enlarged side view of the illustrative wound coil portion of the stent of FIG. 7A, in a collapsed state.

FIGS. 7A–7C depict an alternative embodiment in which the collapsible portion 206 of the ureteral stent 200 includes a wound coil 700 instead of a mesh portion 500. The wound coil 700 behaves similarly to the mesh portion 500, in that under radial force from the intramural tunnel region 122 of the ureter 102, the wound coil 700 flattens out to close off the lower portion of the ureter 102 and thus prevent urine back flow to the kidney 106. FIG. 7A depicts one illustrative embodiment in which the wound coil 700 extends from the bladder end 214 of the elongated portion 202. In FIG. 7A, the wound coil 700 is depicted in an open and expanded state. FIG. 7B is a longitudinal, cross-sectional view of the collapsible portion 206 of the ureteral stent of FIG. 7A in an open and expanded state. As shown, the wound coil 700 forms a lumen 702 which extends from the internal lumen 400 of the elongated portion 202. FIG. 7C is an illustrative embodiment featuring the wound coil 700 in a collapsed state. As discussed above, the wound coil 700 collapses, for example, due to radial force exerted on the exterior of the wound coil 700 and inhibits fluid flow through the lumen 702. In response to the radial force being removed, the radial wound coil 700 returns to the expanded and open state.

Figure 8A:
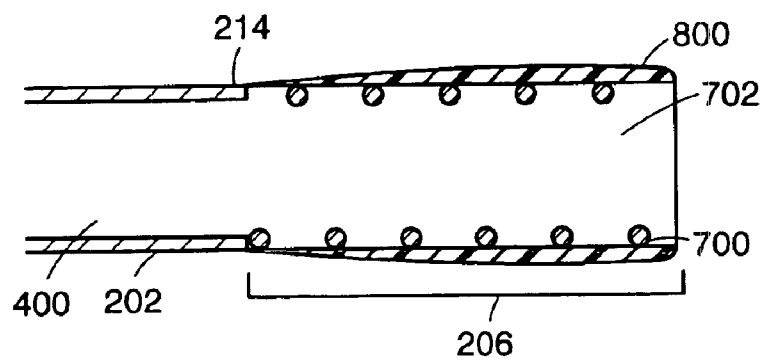
FIG. 8A is a longitudinal, cross-sectional view, according to an illustrative embodiment of the wound coil portion of FIG. 7A, including an outer covering.
Figure 8B:
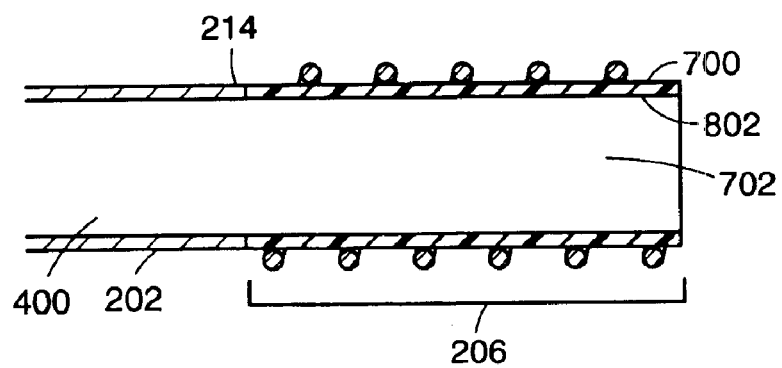
FIG. 8B is a longitudinal, cross-sectional view, according to an illustrative embodiment of the wound coil portion of FIG. 7A, including an inner lining.
Figure 8C:
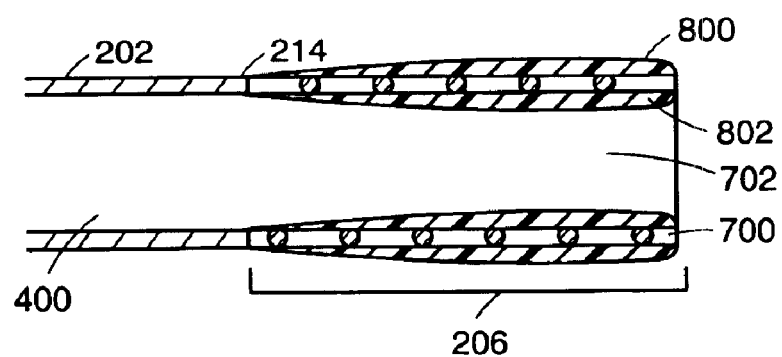
FIG. 8C is a longitudinal, cross-sectional view, according to an illustrative embodiment of the wound coil portion of FIG. 7A, including both an inner lining and an outer covering.

FIGS. 8A–8C depict enlarged longitudinal cross-sectional views, further illustrating embodiments of the wound coil 700. As shown in FIG. 8A, the collapsible wound coil 700 has an outer covering 800. In an illustrative embodiment, the outer covering 800 is formed from a flexible polymer such as, for example, polyurethane, polyamide, silicone, polyvinyl chloride, or the like. As shown in FIG. 8B, in a further illustrative embodiment, the wound coil 700 has an inner lining 802, such as, for example, a jacket or a sleeve. In one embodiment, the inner lining 802 encases the interior of the lumen 702 of the wound coil 700. In the illustrative embodiment, the inner lining 802 is fabricated from a polymer such as, for example, polyurethane, polyamide, silicone, polyvinyl chloride, or the like.

In one preferred embodiment of the invention, the wound coil 700 includes both an outer covering 800 as well as an inner lining 802. In the illustrative embodiment, the wound coil 700 is sandwiched between an outer covering 800 and an inner lining 802, which encase the exterior and the interior portions of the wound coil 700 respectively.

Figure 9:
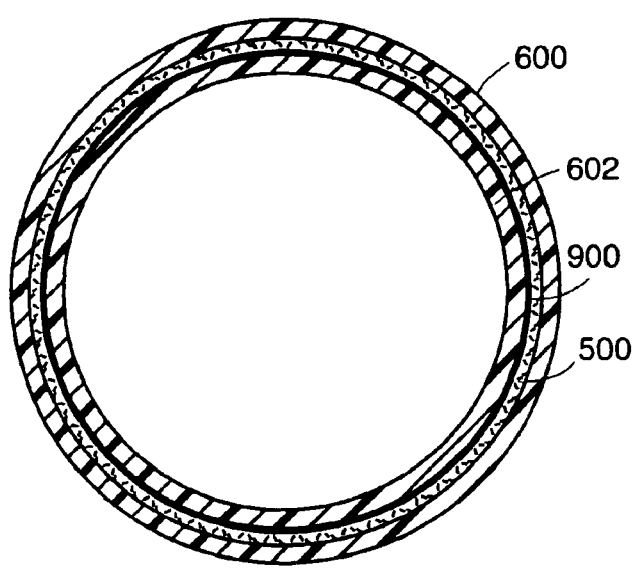
FIG. 9 is a transverse, cross-sectional view of the mesh portion of FIG. 4A, taken along the line B–B' in FIG. 4A.

FIG. 9 is an enlarged, transverse cross sectional end view of the terminal end 416 of the collapsible portion 206 taken along view B–B'. In one preferred embodiment, the collapsible portion 206 has a polymeric ring 900 extending circumferentially around its terminal end 416. According to the illustrative embodiment, the polymeric 900 ring protects, for example, the jagged edges of the mesh portion 500 or wound coil 700 and helps to maintain the shape of the mesh portion 500 or wound coil portion 700 after the ureteral stent 200 is placed within a patient. Preferably, the polymeric ring 900 is made from a thermoplastic polymer. In yet another embodiment, a retention flange is used instead of a polymeric ring.

Figure 10A:
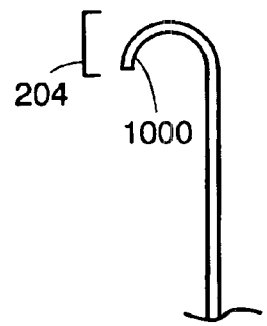
FIG. 10A is a schematic view of the stent of FIG. 2 having a J-shaped kidney retention portion, according to an illustrative embodiment of the invention.
Figure 10B:
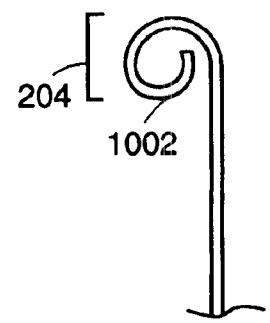
FIG. 10B is a schematic view of the stent of FIG. 2 having a single loop shaped kidney retention portion, according to an illustrative embodiment of the invention.
Figure 10C:
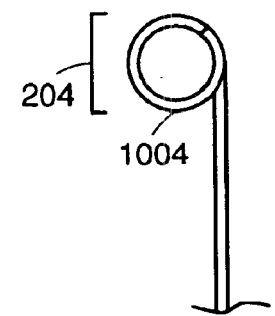
FIG. 10C is a schematic view of the stent of FIG. 2 having a multi loop shaped kidney retention portion, according to an illustrative embodiment of the invention.

FIGS. 10A–10C are conceptual drawings depicting various illustrative embodiments of the retention portion 204. The retention portion 204 of the ureteral stent 200 may be shaped, for example, as a hook, a coil or a malecot, or the like, to facilitate its retention in the kidney 106. In one illustrative embodiment, shown in FIG. 10A, the retention portion 204 of the ureteral stent 200 is shaped like a J hook 1000. In another illustrative embodiment, shown in FIG. 10B, the retention portion 204 of the ureteral stent 200 has a single loop configuration 1002. In a preferred illustrative embodiment of the invention, depicted in FIG. 10C, the retention portion 204 has a multi-loop configuration 1004. In this illustrative embodiment, the multi-loop configuration 1004 allows the ureteral stent 200 to compensate for any changes in the length of the ureter 102 caused by peristalsis in the urinary tract 100. The multi-loop configuration 1004 also enables the accommodation of different ureteral sizes in different size patients.

Various methods are used for inserting the ureteral stent 200 into a patient. In one embodiment of the invention, the retention portion 204 of the ureteral stent 200 is inserted though the urethral opening 114 of a patient, advanced through the bladder 110 and the ureter 102, and subsequently placed in the kidney 106 of the patient. Prior to insertion, the collapsible portion 206 is temporarily collapsed to facilitate insertion into the patient's body. The retention portion 204 is also straightened out prior to insertion.

In yet another embodiment of the invention, a cytoscope is used for inserting the ureteral stent 200 of the invention into a patient. In this embodiment, the ureteral stent 200 is inserted within the cytoscope prior to insertion into the urinary tract 100 and the cytoscope is removed subsequent to proper positioning of the ureteral stent 200 within the patient.

In yet another embodiment, the mesh portion 500 of the ureteral stent 200 is maintained to have a sufficiently large inner diameter, so as to allow passage over a guide wire.

In one aspect of the invention, a method of manufacturing the collapsible mesh portion 500 of the ureteral stent is 200 described. The mesh portion 500 is fabricated from polymeric or metallic materials, such as, for example, stainless steel, tantalum, gold, titanium, nitinol, polytetrafluoroethylene (PTFE) or any suitable plastic material that is collapsible when formed and radially expandable.

The mesh portion 500 can be of any design or configuration and is made in any manner described in the art. In one embodiment of the invention, the mesh is braided in a "2 over-2 under" helical pattern. The mesh braid is then laminated over the bladder end 214 of the elongated portion 202 of the ureteral stent 200.

In another embodiment, individual mesh strands are attached to each other via thermal bonding, in the case of polymeric materials, or via resistance welding or use of an adhesive in the case where metallic elements are utilized.

In yet another embodiment, the braided mesh is braided directly over the bladder end 214 of the ureteral stent 200 using a pre-heat step to embed the braid onto the bladder end 214. In another aspect of the invention, ureteral stent 200 is prepared by hollowing out a metal pipe to leave a stent skeleton. Exemplary processes known in the art for preparation of the ureteral stent 200, include an etching process, also known as photo-fabrication; processes that employ masks and chemicals; electric discharge machining processes; and mechanical machining processes or stamping an open-cell pattern into a solid tube which is usually made of a polymeric material.

A ureteral stent 200 is used to treat ureteral blockage for proper drainage of fluids between the kidney 106 and the bladder 110. Treatment of ureteral blockage is provided, for example, by inserting a ureteral stent 200 over a guide wire with a pusher through the urethral opening 114 and into the bladder 110. The guide wire or a cannula is used temporarily to straighten out the retention portion 204 of the ureteral stent 200. The retention portion 204 of the uretral stent 200 is typically made from material that is able to regain its structure after distortion which allows for the retention portion 204 to be straightened out prior to placement within the body.

In one aspect of the invention, a method for treating ureteral blockage in a patient includes sliding the ureteral stent 200 over a guide wire. The guidewire is inserted into the body of a patient through the bladder 110 and into the ureter 102. A ureteral stent 200 is subsequently slid over the guide wire, such that one end of the guide wire is inserted through the kidney end 212 of the ureteral stent 200. The ureteral stent 200 is moved along the length of the guide wire by the use of a pusher which includes a lumen to accept a guide wire.

In a preferred embodiment of the invention, the collapsible mesh portion 500 maintains a sufficiently large inner diameter so as to allow passage over a 0.035"/0.038" guide wire. In one embodiment, the ureteral stent 200 is tracked over the wire for positioning inside the body using conventional methods of placement such as a pusher to abut the retention portion 204 of the ureteral stent 200.

Variations, modifications, and other implementations of what is described herein will occur to those of ordinary skill in the art without departing from the spirit and the scope of the invention. This invention is not limited to the preceding illustrative description.

What is claimed is:

1. A ureteral stent for facilitating drainage from a kidney of a patient to a bladder of the patient, the ureteral stent comprising:

an elongated portion having first and second ends defining a first portion of an internal lumen extending therebetween, and having a length sufficient to extend substantially within a ureter of the patient from the kidney to the bladder of the patient, the elongated portion not having a mesh construction;

a retention portion extending from the first end of the elongated portion, defining a second portion of the lumen, and defining at least one through aperture for providing fluid communication between the lumen and the kidney, the second portion extending from the first portion and the retention portion being adapted for placement substantially within the kidney; and a mesh portion extending from the second end of the elongated portion, the mesh portion being adapted for placement substantially within an intramural tunnel portion of the ureter and for extending into the bladder and being collapsible under radial compression from the intramural tunnel portion.

2. The stent of claim 1, wherein the mesh portion includes an outer covering.

3. The stent of claim 2, wherein the outer covering includes a polymer.

4. The stent of claim 3, wherein the polymer comprises a material selected from the group consisting of polyurethane, polyamide, silicone, and polyvinyl chloride.

5. The stent of claim 1, wherein the mesh portion includes an inner lining.

6. The stent of claim 1, wherein the mesh portion includes a resilient material.

7. The stent of claim 1, wherein the retention portion includes a J-shaped hook portion.

8. The stent of claim 1, wherein the retention portion includes at least one loop portion.

9. The ureteral stent of claim 1, wherein the elongated portion defines a plurality of opening between the first end of the elongated portion and the second end of the elongated portion, each of the plurality of openings is in fluid communication with the lumen.

10. A ureteral stent for facilitating drainage in a urinary system of a patient, the ureteral stent comprising:

an elongated portion extending from a first point to a second point and defining a first portion of an internal lumen extending between the first point and the second point, the elongated portion having a length sufficient to extend substantially within a ureter of the patient from a kidney to a bladder of the patient, the elongated portion not having a mesh construction; and a mesh portion extending from the second point of the elongated portion, the mesh portion being adapted for placement substantially within an intramural tunnel portion of a ureter and for extension into a bladder of the patient and being collapsible under radial compression from the intramural tunnel portion.

11. The stent of claim 10, wherein the mesh portion includes an outer covering.

12. The stent of claim 11, wherein the outer covering includes a polymer.

13. The stent of claim 12, wherein the polymer comprises a material selected from the group consisting of polyurethane, polyamide, silicone, and polyvinyl chloride.

14. The stent of claim 10, wherein the mesh portion includes an inner lining.

15. The stent of claim 10, wherein the mesh portion includes a resilient material.

16. The ureteral stent of claim 10, wherein the elongated portion defines a plurality of openings between the first end of the elongated portion and the second point of the elongated portion, each of the plurality of openings is in fluid communication with the lumen.

17. A ureteral stent for facilitating drainage from a kidney of a patient to a bladder of the patient, the ureteral stent comprising:
- an elongated portion having first and second ends defining a first portion of a lumen extending therebetween, and having a length sufficient to extend substantially within a ureter from the kidney to the bladder of the patient;
- a retention portion extending from the first end of the elongated portion, defining a second portion of the lumen, and defining at least one through aperture for providing fluid communication between the lumen and the kidney, the second portion extending from the first portion, and the retention portion being adapted for placement substantially within the kidney; and
- a coil portion extending from the second end of the elongated portion and comprising a wound coil, the wound coil portion being adapted for placement substantially within an intramural tunnel portion of the ureter and for extension into the bladder, the coil portion being sized and configured to be collapsible under radial compression from the intramural tunnel portion.

18. The stent of claim 17, wherein the wound coil includes an outer covering.

19. The stent of claim 18, wherein the outer covering includes a polymer.

20. The stent of claim 19, wherein the polymer comprises a material selected from the group consisting of polyurethane, polyamide, silicone, and polyvinyl chloride.

21. The stent of claim 17, wherein the wound coil includes an inner lining.

22. The stent of claim 17, wherein the retention portion includes a J-shaped hook portion.

23. The stent of claim 17, wherein the retention portion includes at least one loop portion.

24. A ureteral stent for facilitating drainage in a urinary system of a patient, the ureteral stent comprising:
- an elongate portion not having a mesh construction; and
- a wound coil portion adapted for placement substantially within an intramural tunnel portion of a ureter of the patient and for extension into a bladder of the patient, the coil portion being sized and configured to be collapsible under radial compression from the intramural tunnel portion, the coil portion extending from the elongate portion.

25. The stent of claim 24, wherein the wound coil includes an outer covering.

26. The stent of claim 25, wherein the outer covering includes a polymer.

27. The stent of claim 26, wherein the polymer comprises a material selected from the group consisting of polyurethane, polyamide, silicone, and polyvinyl chloride.

28. The stent of claim 24, wherein the wound coil includes an inner lining.

29. A method of placing a ureteral stent in a patient, the method comprising:
- providing a ureteral stent comprising:
  - an elongated portion having first and second ends defining a first portion of a lumen extending therebetween, and having a length sufficient to extend substantially within a ureter of the patient from a kidney of the patient to a bladder of the patient, the elongated portion not having a mesh construction;
  - a retention portion extending from the first end of the elongated portion, defining a second portion of the lumen, and defining at least one through aperture for providing fluid communication between the lumen and the kidney, the second portion extending from the first portion and the retention portion being adapted for placement substantially within the kidney; and
  - a mesh portion extending from the second end of the elongated portion, the mesh portion being adapted for placement substantially within an intramural tunnel portion of the ureter and for extension into the bladder and being collapsible under radial compression from the intramural tunnel portion;
- inserting the ureteral stent into the ureter of the patient; and
- positioning the ureteral stent in the patient with the retention portion substantially within the kidney of the patient and the mesh portion substantially within the intramural tunnel portion of the ureter and extending into the bladder.

30. A method of placing a ureteral stent in a patient, the method comprising:
- providing a ureteral stent comprising:
  - an elongated portion having first and second ends defining a first portion of a lumen extending therebetween, and having a length sufficient to extend substantially within a ureter of the patient from a kidney to a bladder of the patient;
  - a retention portion extending from the first end of the elongated portion, defining a second portion of the lumen, and defining at least one through aperture for providing fluid communication between the lumen and the kidney, the second portion extending from the first portion and the retention portion being adapted for placement substantially within the kidney; and
  - a coil portion extending from the second end of the elongated portion and including a wound coil, the wound coil being adapted for placement substantially within an intramural tunnel portion of the ureter and for extension into the bladder, the coil portion being sized and configured to be collapsible under radial compression from the intramural tunnel portion;
- inserting the ureteral stent into the ureter of the patient; and
- positioning the ureteral stent in the patient with the retention portion substantially within the kidney of the patient and the wound coil substantially within the intramural tunnel portion of the ureter and extending into the bladder.

31. A ureteral stent for facilitating drainage from a kidney of a patient to a bladder of the patient, the ureteral stent comprising:
- an elongated portion having first and second ends defining a first portion of a lumen extending therebetween, and having a length sufficient to extend substantially within a ureter from the kidney to the bladder of the patient, the elongated portion not having a coiled construction;

a retention portion extending from the first end of the elongated portion, defining a second portion of the lumen, and defining at least one through aperture for providing fluid communication between the lumen and the kidney, the second portion extending from the first portion, and the retention portion being adapted for placement substantially within the kidney; and a coil portion extending from the second end of the elongated portion and comprising a wound coil, the wound coil portion being adapted for placement substantially within an intramural tunnel portion of the ureter and for extension into the bladder and being collapsible under radial compression from the intramural tunnel portion.

32. The stent of claim 31, wherein the wound coil includes an outer covering.

33. The stent of claim 30, wherein the outer covering includes a polymer.

34. The stent of claim 31, wherein the polymer comprises a material selected from the group consisting of polyurethane, polyamide, silicone, and polyvinyl chloride.

35. The stent of claim 31, wherein the wound coil includes an inner lining.

36. The stent of claim 31, wherein the retention portion includes a J-shaped hook portion.

37. The stent of claim 31, wherein the retention portion includes at least one loop portion.

* * * * *

UNITED STATES PATENT AND TRADEMARK OFFICE
CERTIFICATE OF CORRECTION

PATENT NO. : 6,887,215 B2  
APPLICATION NO. : 10/006083  
DATED : May 3, 2005  
INVENTOR(S) : John O. McWeeney Page 1 of 1

It is certified that error appears in the above-identified patent and that said Letters Patent is hereby corrected as shown below:

In claim 9, column 8, line 44 delete "opening" and add --openings--
In claim 16, column 9, line 9 delete "end" and add --point--

Signed and Sealed this

Fifth Day of February, 2008

JON W. DUDAS
*Director of the United States Patent and Trademark Office*